US009687318B2

(12) United States Patent
Carriere Lluch et al.

(10) Patent No.: US 9,687,318 B2
(45) Date of Patent: Jun. 27, 2017

(54) BASE FOR AN ORTHODONTIC APPLIANCE

(71) Applicant: ORTHODONTIC RESEARCH AND DEVELOPMENT, S.L., Barcelona (ES)

(72) Inventors: Luis Carriere Lluch, Barcelona (ES); Jose Carriere Pons, Barcelona (ES)

(73) Assignee: ORTHODONTIC RESEARCH AND DEVELOPMENT, S.L., Barcelona (ES)

( * ) Notice: Subject to any disclaimer, the term of this patent is extended or adjusted under 35 U.S.C. 154(b) by 442 days.

(21) Appl. No.: 14/356,600

(22) PCT Filed: Nov. 8, 2012

(86) PCT No.: PCT/EP2012/072124
§ 371 (c)(1),
(2) Date: May 6, 2014

(87) PCT Pub. No.: WO2013/068456
PCT Pub. Date: May 16, 2013

(65) Prior Publication Data
US 2014/0302450 A1    Oct. 9, 2014

(30) Foreign Application Priority Data
Nov. 8, 2011   (EP) ..................................... 11382340

(51) Int. Cl.
*A61C 7/28*  (2006.01)
*A61C 7/16*  (2006.01)
*A61C 7/14*  (2006.01)

(52) U.S. Cl.
CPC ................ *A61C 7/282* (2013.01); *A61C 7/14* (2013.01); *A61C 7/16* (2013.01)

(58) Field of Classification Search
CPC .............. A61C 7/282; A61C 7/14; A61C 7/16
See application file for complete search history.

(56) References Cited

U.S. PATENT DOCUMENTS 3,975,824 A * 8/1976 Lee .......................... A61C 7/287
                                                                    433/14
4,604,057 A * 8/1986 Viglietti .................... A61C 7/16
                                                                    433/9

(Continued)

FOREIGN PATENT DOCUMENTS

DE           44 34 209         3/1996
WO    WO 2009/094685      8/2009

OTHER PUBLICATIONS

International Search Report for PCT/EP2012/072124, mailed Feb. 27, 2013, 13 pgs.

*Primary Examiner* — Cris L Rodriguez
*Assistant Examiner* — Hao D Mai
(74) *Attorney, Agent, or Firm* — Squire Patton Boggs (US) LLP

(57) ABSTRACT

Base for an orthodontic appliance includes a base surface adapted to be attached to a tooth and a plurality of protrusions protruding from the base surface and extending along a first direction substantially from a first edge of the base surface to a second edge of the base surface, a second direction being defined as perpendicular to the base surface, wherein the distance between two of the protrusions in a plane substantially perpendicular to the first direction along at least a portion of the protrusions is smaller than the distance between the two protrusions at the base surface, and wherein the distance between two of the protrusions in planes substantially perpendicular to the second direction at the first edge and the second edge is larger than a distance between the two protrusions in a plane between the first and the second edge.

20 Claims, 6 Drawing Sheets

(56) References Cited

U.S. PATENT DOCUMENTS

| | | | |
|---|---|---|---|
| D290,040 S * | 5/1987 | Kelly | D24/180 |
| 4,676,746 A * | 6/1987 | Klapper | A61C 7/12 433/16 |
| 4,936,773 A * | 6/1990 | Kawaguchi | A61C 7/12 433/8 |
| 5,071,344 A * | 12/1991 | Wong | A61C 7/16 433/228.1 |
| 5,095,602 A * | 3/1992 | Reher | A61C 7/14 29/896.11 |
| 5,267,854 A * | 12/1993 | Schmitt | A61C 7/16 433/8 |
| 5,295,823 A | 3/1994 | Farzin-Nia | |
| 5,441,408 A * | 8/1995 | Moschik | A61C 7/12 433/8 |
| D373,638 S * | 9/1996 | Colbert | D24/180 |
| 5,616,026 A * | 4/1997 | Cash | A61C 7/14 433/8 |
| 5,681,165 A * | 10/1997 | Feldman | A61C 7/30 433/8 |
| 5,711,665 A * | 1/1998 | Adam | A61C 19/004 433/24 |
| 5,820,371 A | 10/1998 | Forster | |
| 6,190,165 B1 * | 2/2001 | Andreiko | A61C 7/16 433/9 |
| 6,444,167 B1 * | 9/2002 | Shimodaira | A61C 7/16 419/37 |
| 6,464,494 B1 * | 10/2002 | Young | A61C 7/10 433/18 |
| 7,845,941 B2 * | 12/2010 | Minium | A61C 7/12 433/16 |
| 8,251,696 B2 * | 8/2012 | Rodriguez | A61C 7/30 433/10 |
| 2005/0069833 A1 * | 3/2005 | Chikami | A61C 7/20 433/9 |
| 2006/0263736 A1 * | 11/2006 | Moon | A61C 7/16 433/9 |
| 2007/0166658 A1 | 7/2007 | Voudouris | |
| 2008/0138756 A1 * | 6/2008 | Lim | A61C 7/14 433/10 |
| 2008/0160474 A1 * | 7/2008 | Wolf | A61C 7/14 433/10 |
| 2009/0117512 A1 | 5/2009 | Minium | |
| 2009/0325117 A1 * | 12/2009 | Cervera Sabater | A61C 7/14 433/10 |
| 2010/0285421 A1 * | 11/2010 | Heiser | A61C 7/285 433/11 |
| 2011/0086323 A1 * | 4/2011 | Wessinger | A61C 7/14 433/11 |
| 2011/0189623 A1 * | 8/2011 | Moon | A61C 7/16 433/9 |
| 2011/0195371 A1 * | 8/2011 | Hirsch | A61C 7/28 433/10 |
| 2012/0315593 A1 * | 12/2012 | Ramos-de-la-Pena | A61C 7/14 433/9 |
| 2013/0236847 A1 * | 9/2013 | Shin | A61C 7/16 433/3 |
| 2015/0037747 A1 * | 2/2015 | Choi | A61C 7/28 433/9 |
| 2016/0000530 A1 * | 1/2016 | Hagelganz | A61C 7/16 433/9 |

* cited by examiner

BASE FOR AN ORTHODONTIC APPLIANCE

This application claims the benefit of European Patent Application EP11382340.5 filed on 8 Nov. 2011, which is hereby incorporated in its entirety by reference.

The present invention relates to a base for an orthodontic appliance. It further relates to an orthodontic appliance comprising such a base.

BACKGROUND ART

Many different orthodontic appliances are known to correct malocclusions, such as e.g. crowns, bridges, brackets, distalizers and retainers. Some of these appliances may in use be attached to the surface of a tooth or various teeth in order to correct the orientation or position of one or more teeth. Depending on their function they may be attached on the lingual or labial surface of an incisor, canine, premolar or molar.

Examples of orthodontic appliances that may be attached to teeth include of course the well known brackets, but also e.g. distalizers such as known from e.g. US 2006/018833, and also e.g. buccal tubes, molar tubes, lingual buttons and others.

For their attachment to a tooth or various teeth, an orthodontic appliance may comprise one or more base surfaces which may be adapted to fit to a particular tooth or one of a plurality of teeth. This base surface may be substantially flat or may be concave to adapt to the specific tooth it needs to be attached to.

Before attachment, the surface of the tooth may be cleaned, possibly etched and subsequently dried. Then, an adhesive may be applied to the surface of the tooth. It is known to use an adhesive which may be activated using light. The orthodontic appliance, possibly also comprising an adhesive on its base surface may then be attached to the surface of the tooth. After activation of the adhesive using e.g. light, the orthodontic appliance may be firmly fixed to the tooth. Different types of adhesives may be used, such as e.g. composite resins or glass ionomer cement. This process is also referred to as "bonding", or, depending on the adhesive used "cement bonding".

The orthodontic appliance may stay bonded to a tooth by chemical bonding forces and/or mechanical retention forces. Depending on the base of the orthodontic appliance, specifically its shape and material, chemical bonding or mechanical retention may be dominant. For example, metallic appliances generally have limited chemical bonding. They rely mostly on mechanical retention. In this context, it is known to provide a base surface with a certain roughness or a plurality of protrusions that are adapted to retain the appliance on the tooth in a mesial-distal direction and a lingual-labial direction.

However, there still exists a need to provide an orthodontic appliance which in use is attached to a surface of a tooth that provides good mechanical retention in the lingual-labial direction, the mesial-distal direction, and the mandible-maxilla direction (up and down) and is easy to manufacture.

SUMMARY

According to a first aspect, an orthodontic appliance is provided that comprises a base surface adapted to be attached to a tooth and a plurality of protrusions protruding from said base surface and extending in a first direction substantially from a first edge of the base surface to a second edge of the base surface. A second direction may be defined as perpendicular to said base surface, and a third direction may be defined as perpendicular to said first and said second direction. In this aspect, the distance (as measured along the third direction) between two of said protrusions in a plane substantially perpendicular to said first direction along at least a portion of said protrusions is smaller than the distance (as measured along the third direction) between said two protrusions at the base surface. Furthermore, the distance (as measured along the third direction) between two of said protrusions in any plane substantially perpendicular to said second direction at said first edge and said second edge is larger than the distance between said two protrusions in the same plane at a point between said first and said second edge.

In this aspect, an orthodontic appliance is provided that due to the shape of the protrusions provides mechanical retention once attached to the teeth in three directions. Firstly due to the arrangement of various protrusions extending in a first direction (e.g. up-down) next to each other, mechanical retention is provided in the mesial-distal direction. Due to the shape of the protrusions, mechanical retention may be provided both in the lingual-labial direction and the mandible-maxilla direction (i.e. up-down). Furthermore, due to the distance between the protrusions being at least as large at the edges than at a more central portion, the appliance may be easily manufactured using e.g. injection moulding or micro-injection moulding. However, it should be noted that embodiments of the present invention may also be manufactured using machining techniques such as e.g. milling.

As noted before, the base surface may be concave in e.g. the first and/or third direction. As such, the first direction and/or third direction may be curved. Thus, the vector representing the first, third and second direction may change from point to point on such a concave surface. Herein, the first, second and third direction are to be understood as the directions determined locally from a point on the base surface.

In some embodiments, all protrusions may be substantially identical. In other embodiments, the protrusions do not necessarily all need to be the same.

In some embodiments, one or more of the protrusions along its length has a linearly varying cross-section in planes substantially perpendicular to said first direction. In particular, the width may vary linearly along the length of the protrusion. These embodiments may be relatively easily manufactured. Alternatively, one or more of the protrusions along its length has a non-linearly varying cross-section in planes substantially perpendicular to said first direction.

In some embodiments, said protrusions have the widest cross-section in planes substantially perpendicular to said first direction substantially midway between said first and said second edge. In these cases, two negative moulds may be used for manufacturing. The split between these moulds may be substantially midway between the first and second edge. In alternative embodiments, the split between two negative moulds does not need to be midway between the first and second edge. If the distance between the protrusions is substantially larger at the edges than at a central portion, the moulds may be easily retracted after moulding.

In some embodiments, one or more of said protrusions have a dovetail cross-section in planes substantially perpendicular to said first direction. The dovetail cross-section is well known in the field, may be easily manufactured and provides good mechanical retention. In some other embodiments, one or more of said protrusions have a bulged cross-section in planes substantially perpendicular to said first direction. In yet other embodiments, the protrusions may comprise locally increased widths at one or more heights.

In some embodiments, the orthodontic appliance may be metallic. However, in other embodiments, polymers may be used. For example, the use of e.g. polysulfones is well known in the field. In yet further embodiments, ceramics may be used or fibre-reinforced composites. Regardless of the material used, the shape and arrangement of the protrusions may ensure sufficient bonding to the teeth.

In a further aspect, a bracket with a base such as substantially hereinbefore described is provided. The base may be manufactured integrally with the bracket, or may be manufactured separately and subsequently attached to a main body of a bracket.

In another aspect, a distalizer comprising a base such as substantially hereinbefore described is provided. In other implementations, other auxiliary orthodontic elements comprising such a base may be provided, such as e.g. buccal tubes, molar tubes and lingual buttons.

In yet another aspect, a base for an orthodontic appliance is provided that comprises a first flat surface for attachment to the main body of an orthodontic appliance and further comprising a base surface adapted to be attached to a tooth. A plurality of protrusions protrude from said base surface and extend substantially from a first edge of the base surface to a second edge of the base surface along a first direction. A second direction may be defined as perpendicular to said base surface, and a third direction may be defined as perpendicular to said first and said second direction. In accordance with this aspect, the distance (as measured along the third direction) between two of said protrusions in a plane substantially perpendicular to said first direction along at least a portion of said protrusions is smaller than the distance between said two protrusions at the base surface, and the distance between two of said protrusions in any plane substantially perpendicular to said second direction at said first edge and said second edge is larger than the distance between said two protrusions in the same plane at a point between said first and said second edge.

In yet a further aspect, an orthodontic appliance is provided that comprises a base surface with protrusions that are arranged and shaped such that three-dimensional mechanical retention is provided.

Additional objects, advantages and features of embodiments of the invention will become apparent to those skilled in the art upon examination of the description, or may be learned by practice of the invention.

BRIEF DESCRIPTION OF THE DRAWINGS

Particular embodiments of the present invention will be described in the following by way of non-limiting examples, with reference to the appended drawings, in which.

DETAILED DESCRIPTION OF EMBODIMENTS

Figure 5:
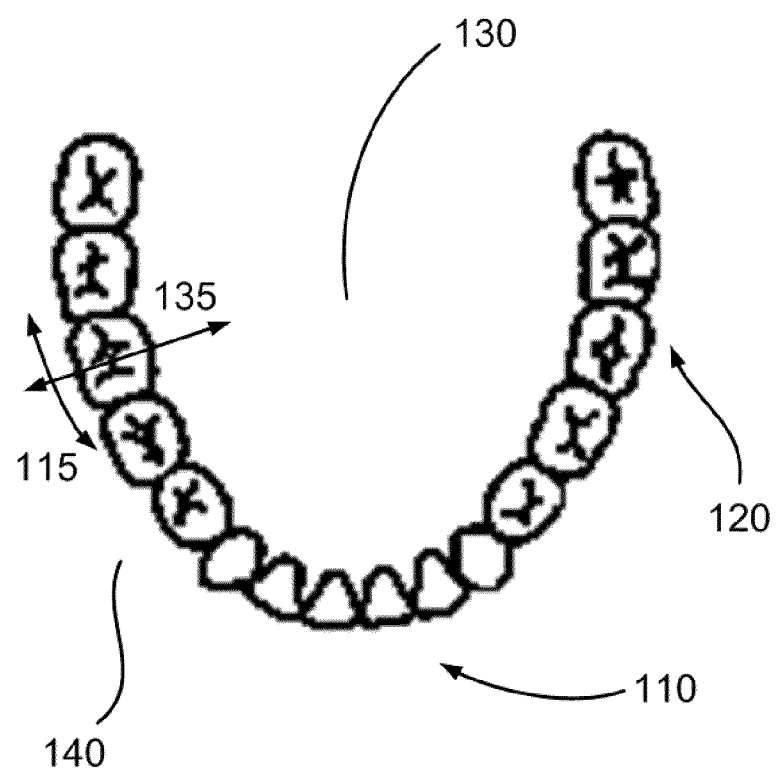
FIG. 5 explains some of the terminology used herein.

FIG. 5 shows schematically the arrangement of teeth in the lower jaw (mandible). A front portion of the mouth 110 may be referred to as a mesial region. A rear portion of the mouth 120 may be referred to as a distal region. An inner portion of the mouth behind the teeth 130 may be referred to as a lingual region. An outer portion of the mouth 140 may be referred to as a labial region. A mesial-distal direction 115 with respect to a specific tooth (first molar) has been schematically indicated in FIG. 5. Also indicated in FIG. 5 is a lingual-labial direction 135 with respect to the same tooth. This terminology will be adhered to in the present disclosure.

Figure 1A:
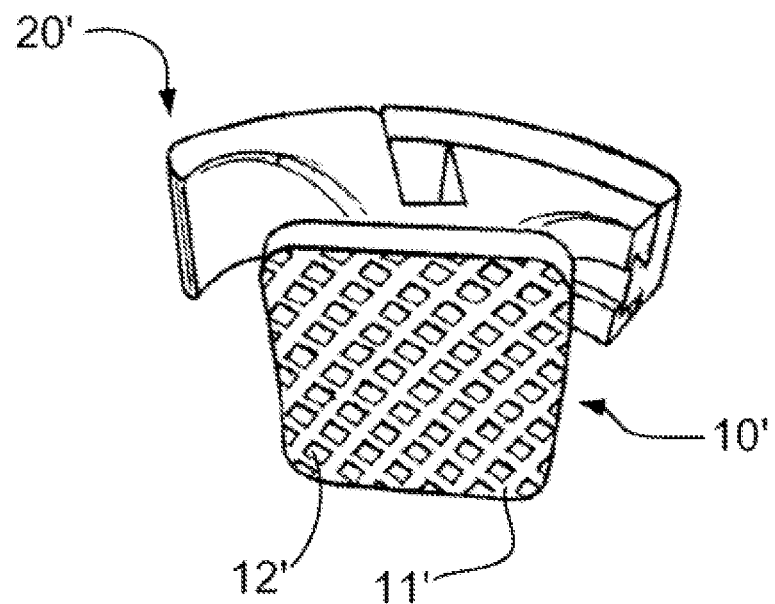
FIG. 1a illustrates a prior art bracket with a prior art base surface for attachment to a tooth.

FIG. 1a illustrates a prior art bracket 20' having a base 10'. The base may be integrally manufactured with the bracket or may be separately manufactured and subsequently attached to the main body of the bracket. The base 10' comprises a base surface 11' which may be slightly concave and may be adapted to fit on a specific tooth. For example, the width and length of the base surface, as well as its concavity may be adapted to fit on a specific tooth or various teeth.

Such a bracket may be firmly attached to a tooth using well known techniques employing adhesives. In order to increase the retention on the tooth, a certain roughness may be provided on the base surface. As the adhesive is spread in between the ridges and recesses of such a rough surface, the mechanical retention may be improved.

In the example shown, a large plurality of small bumps 12' is provided in order to enhance the mechanical retention of the bracket on a tooth.

Figure 1B:
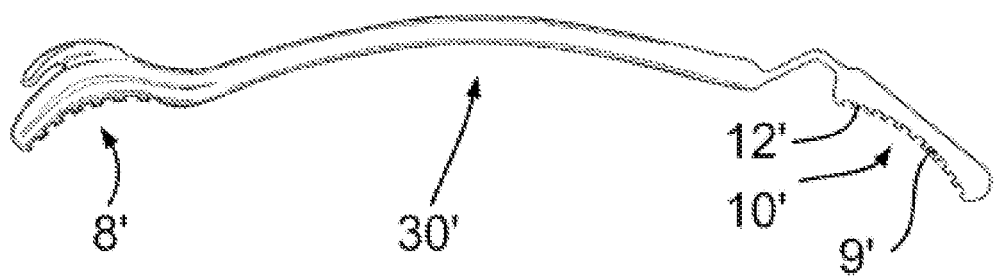
FIG. 1b illustrates a prior art distalizer with a prior art base surface for attachment to a tooth.

FIG. 1b illustrates a prior art distalizer 30', with a first base 9' for attachment to a canine, and a second base 8' for attachment to a molar. Each of the base surfaces comprises a plurality of longitudinal protrusions 12' extending substantially in an up-down direction (when fitted on the tooth). In the example shown, the protrusions have a substantially dovetail shaped cross-section.

Figure 2A:
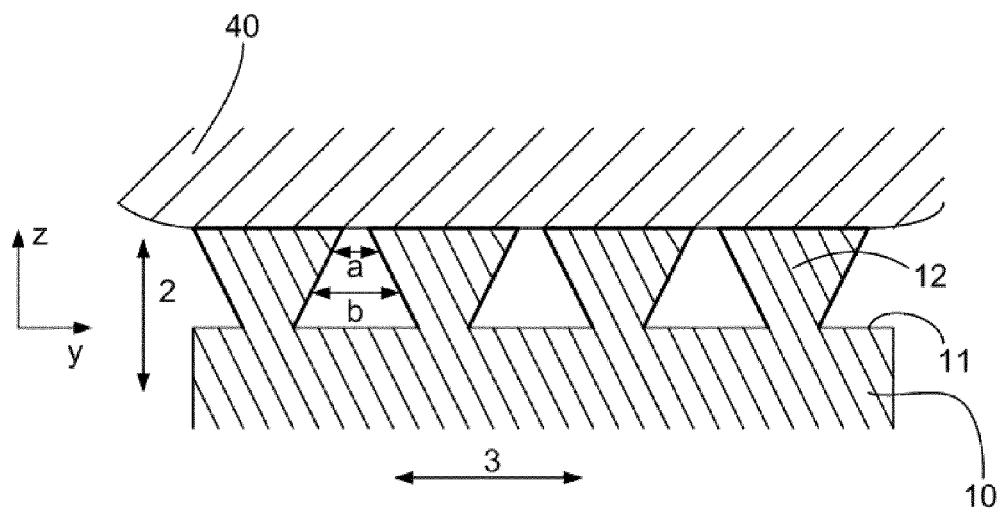
FIGS. 2a and 2b illustrate an orthodontic appliance according to a first embodiment.
Figure 2B:
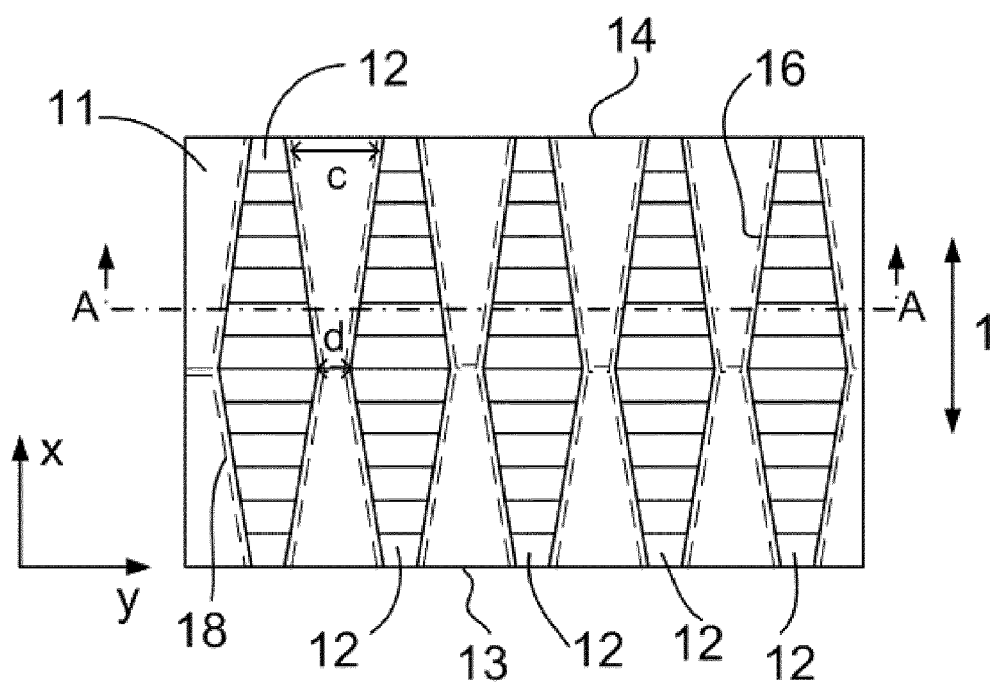

FIGS. 2a and 2b illustrate an orthodontic appliance according to a first embodiment. A plurality of protrusions 12 are provided on base surface 11, which in this case is shown to be substantially flat. The base surface may also be more or less concave such as to be adapted to fit on a specific tooth.

The protrusions extend in a first direction 1 (x-direction) from a first edge 13 to a second edge 14 of the base. The x-direction may correspond to the up-down direction when fitted on a tooth 40. A second direction 2 may be defined as perpendicular to the base surface. This direction corresponds to the z-direction shown in FIG. 2a. In practice, this second direction may thus correspond to the labial-lingual direction. Further, a third direction 3 (y-direction) may be defined as perpendicular to both the first and second direction.

The length of the protrusion may be defined as the dimension of the protrusion in the first direction. Its height may be defined as its dimension in the second direction, and its width may be defined as its dimension in the third direction.

FIG. 2a shows a cross-sectional view along line A-A indicated in FIG. 2b in a plane that is substantially perpendicular to the first direction. As may be seen in FIG. 2a, the cross-section of the protrusion in said plane is substantially dovetail shaped. An aspect of the dovetail shape is that the distance, b, between two neighbouring protrusions close to the base surface 11 is larger than the distance, a, between two neighbouring protrusions further away from base surface 11. This has the effect that, once bonded to the surface of a tooth 40, the protrusions provide mechanical retention in the second direction (lingual-labial). Additionally, since a plurality of protrusions is provided next to each other, also mechanical retention in a third direction 3 (mesial-distal) is provided.

In this case, the minimum distance between two neighbouring protrusions is reached at the top of the protrusion. It should be noted however that this does not necessarily need to be the case in order to provide mechanical retention in the second direction.

FIG. 2b illustrates a top view of the protrusions. The base surface indicated in this figure is substantially rectangular. In practice the base surface does not need to be rectangular, and may instead have curved edges or a combination of curved and straight edges.

It may be seen in FIG. 2b that the protrusions that extend in direction 1 are further spaced apart at the first edge 13 and second edge 14 than at a central portion of the base surface. The distance, c, between two neighbouring protrusions 12 at edge 14 is larger than the distance, d, substantially in a central plane located midway between those edges. Thus, when adhesive has been spread between the protrusions, mechanical retention is also provided in the first direction 1 (i.e. in this example up-down, or maxilla-mandible direction).

In this example, between the point (or rather, plane) of minimum distance and the edge of maximum distance between protrusions, the width of the protrusions varies linearly.

The orthodontic appliance with such a base may be manufactured easily using e.g. injection moulding or micro-injection moulding. To this end, two negative moulds (or, two halves of a mould) 16 and 18 that meet each other substantially at a plane located midpoint between the first and second edge may be used. Since in this example, such a midpoint corresponds to the point at which the distance between two neighbouring protrusions is minimum, and the distance increases towards the edges, the two moulds may be retracted in the first direction.

Although in the example shown the first direction corresponds to the up-down direction, this first direction may be varied within the scope of the present disclosure. For example, the first direction could be the mesial-distal direction. The second direction in this case would be the lingual-labial direction and the third direction would be the up-down direction.

Figure 2C:
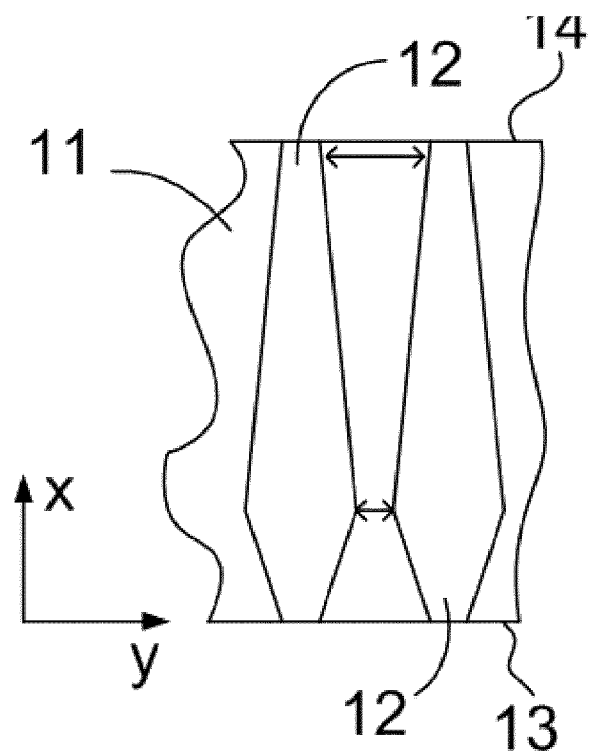
FIG. 2c illustrates the protrusions on a base surface according to further embodiments.

FIG. 2c illustrates the protrusions on a base surface according to further embodiments. FIG. 2c shows a top view of a plurality of protrusions extending in a first direction which in this case corresponds to the previously defined x-direction. FIG. 2c is shown to illustrate that the plane in which the distance between two protrusions 12 is minimum does not need to be midway between the borders 13 and 14. With proper adjustment of the moulds, also the shown shapes can be easily manufactured and the moulds retracted.

Figure 3A:
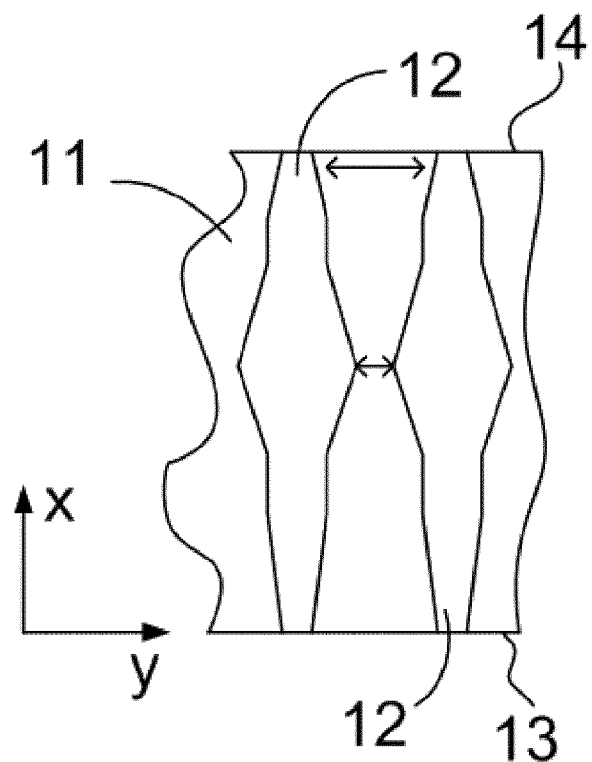
FIGS. 3a-3d illustrate further embodiments of the present invention.

FIGS. 3a-3d illustrate further embodiments of the present invention. FIG. 3a shows a protrusion extending in a first direction from a first edge 13 to a second edge 14 with a varying width. Substantially midway between the edges 13 and 14 a minimum distance is reached. However, contrary to what was shown in FIGS. 2b and 2c, the width of the protrusions varies in a less constant manner. In the case shown in FIG. 3a, in the first direction, there are portions along which the width increases (or decreases) linearly, and portions along which the width is substantially constant.

Since the distance between protrusions from a minimum increases towards the edges, the moulds that may be used for manufacturing may also be easily retracted towards the edges. Even though portions of substantially constant width (and constant distance between protrusions) are shown, in practice these portions may be very slightly angled to facilitate retraction of the moulds.

Figure 3B:
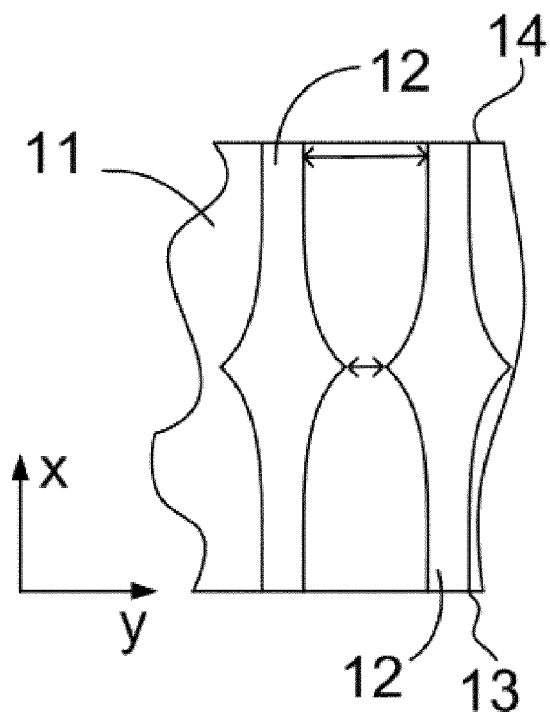

FIG. 3b shows a further embodiment, in which the width of the protrusions is varied in a non-linear manner. It will be clear that also in this embodiment, mechanical retention may be provided in the first direction (x-direction) and third direction (y-direction). With a suitable cross-section of the protrusion in a plane perpendicular to the first direction (such as e.g. a dovetail shaped cross-section), also retention in the second direction (z-direction) may be obtained.

Figure 3C:
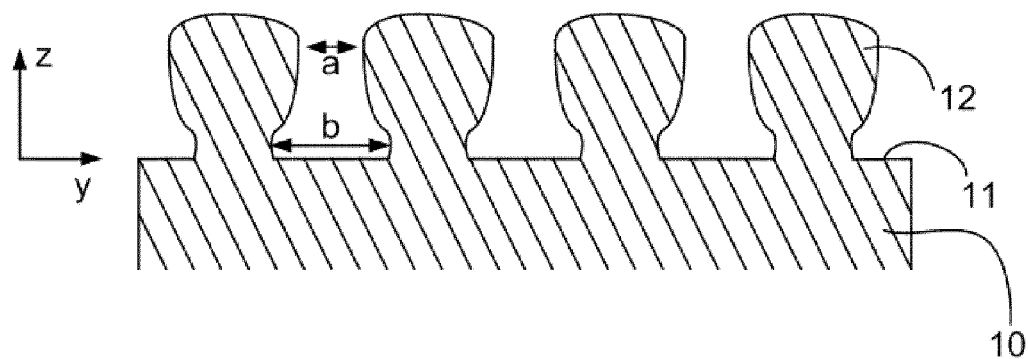

A further possible cross-section in a plane perpendicular to said first direction may be seen in FIG. 3c. Instead of the dovetail shaped cross-section seen in FIG. 2a, a substantially bulged cross-section may also be used. Along the z-direction, the distance between two protrusions decreases with increased distance from the base surface 11 until a minimum is reached near the top of the protrusions. Distance a indicated in FIG. 3c is substantially smaller than distance b. If the width of the protrusion is varied along its length in accordance with one of the previously shown embodiments, mechanical retention may be achieved in three substantially orthogonal directions.

Figure 3D:
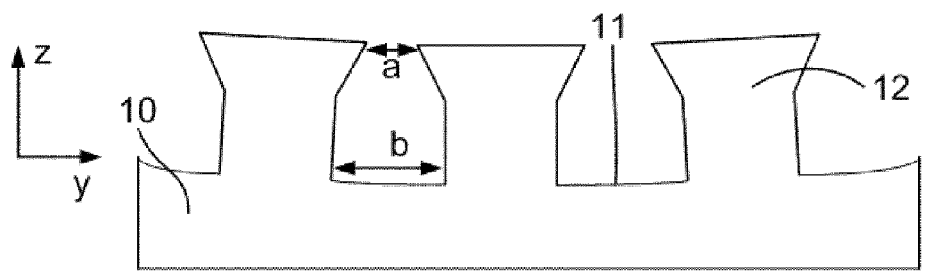

A further embodiment is shown in FIG. 3d. Near a top of the protrusion, a portion of increasing width is provided, such that the distance between neighbouring protrusions at their top is substantially smaller than near the base surface. It is further noted that the distance between neighbouring protrusions is further decreased due to the concavity of the base surface.

It will be clear that further alternative cross-sections may be chosen for the protrusion in order to comply with the prerequisite of mechanical retention in the z-direction.

Figure 4:
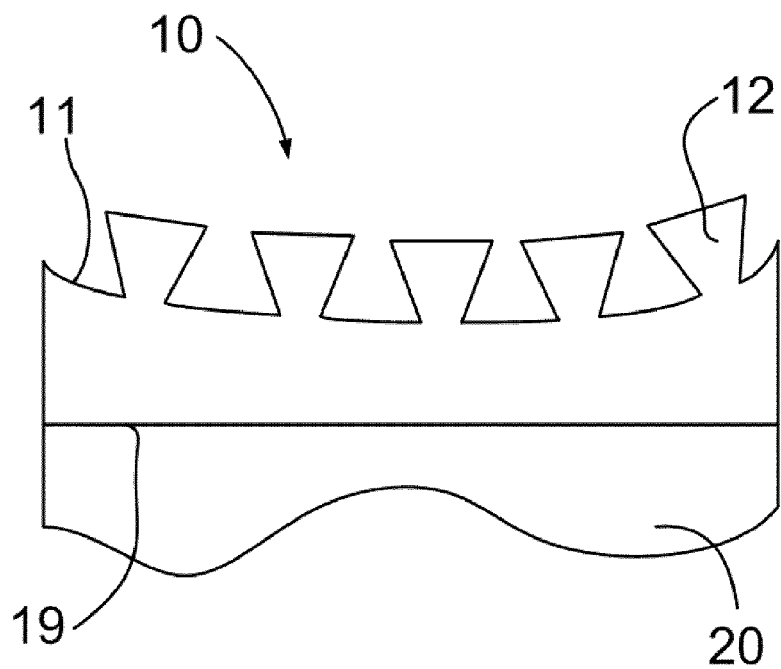
FIG. 4 illustrates a base for an orthodontic appliance according to an embodiment.

FIG. 4 illustrates a base 10 for an orthodontic appliance 20 according to an embodiment. The base 10 may comprise a base surface 11 which may be adapted to be fitted on a tooth, and may be slightly concave. On the opposite side, the base 10 may further comprise a flat surface 19. At this flat surface, the base may be attached to the main body of an orthodontic appliance 20, such as e.g. a bracket.

Although only a number of particular embodiments and examples of the invention have been disclosed herein, it will be understood by those skilled in the art that other alternative embodiments and/or uses of the invention and obvious modifications and equivalents thereof are possible. Furthermore, the present invention covers all possible combinations of the particular embodiments described. Thus, the scope of the present invention should not be limited by particular embodiments, but should be determined only by a fair reading of the claims that follow.

The invention claimed is:

1. An orthodontic appliance, comprising:
a base surface adapted to be attached to a tooth and a plurality of protrusions protruding from the base surface and extending continuously along a first direction substantially from a first edge of the base surface to a second edge of the base surface, wherein channels are formed between neighboring protrusions of the plurality of protrusions and the channels extend continuously from the first edge of the base surface to the second edge of the base surface,
a second direction being defined as perpendicular to the base surface, and a third direction being defined as perpendicular to the first direction and perpendicular to the second direction, wherein for at least protrusions of the plurality of the protrusions, a distance measured along the third direction between the two protrusions in a plane substantially perpendicular to the first direction is smaller than a distance between the two protrusions at the base surface, and wherein a distance measured along the third direction between the two protrusions in a plane substantially perpendicular to the second direction at the first edge and the second edge is larger than a distance between the two protrusions in the same plane at a point between the first edge and the second edge.

2. The orthodontic appliance according to claim 1, wherein all of the plurality of protrusions are substantially identical.

3. The orthodontic appliance according to claim 1, wherein each of the two protrusions has, along its length, a linearly varying cross-section in the plane substantially perpendicular to the first direction.

4. The orthodontic appliance according to claim 3, wherein a width of each of the two protrusions varies linearly.

5. The orthodontic appliance according to claim 1, wherein each of the two protrusions has, along its length, a non-linearly varying cross-section in the plane substantially perpendicular to the first direction.

6. The orthodontic appliance according to claim 4, wherein each of the two protrusions has a widest cross-section in the plane substantially perpendicular to the first direction and the widest cross-section is located substantially midway between the first edge and the second edge.

7. The orthodontic appliance according to claim 1, wherein each of the two protrusions has a bottom proximal the base surface and a top distal the base surface, and wherein a distance between the two protrusions in the plane substantially perpendicular to the first direction is minimum substantially at or near the tops of the two protrusions.

8. The orthodontic appliance according to claim 1, wherein each of the two protrusions has a dovetail cross-section in the plane substantially perpendicular to the first direction.

9. The orthodontic appliance according claim 1, wherein one or more of the plurality of protrusions have a bulged cross-section in the plane substantially perpendicular to the first direction.

10. The orthodontic appliance according to claim 1, wherein each of the plurality of protrusions has a central axis and is arranged such that the central axes are substantially parallel to each other.

11. The orthodontic appliance according to claim 1, wherein the orthodontic appliance is a bracket, a distalizer, a buccal tube, a molar tube or a lingual button.

12. The orthodontic appliance according to claim 1, wherein the base surface is substantially concave.

13. The orthodontic appliance according to claim 1, made of any of the following materials: metals, metal alloys, fiber reinforced composites, ceramics or polymers.

14. A base for an orthodontic appliance, comprising:
a first flat surface for attachment to a main body of an orthodontic appliance and further comprising a base surface adapted to be attached to a tooth and a plurality of protrusions protruding from the base surface and extending continuously along a first direction substantially from a first edge of the base surface to a second edge of the base surface, wherein channels are formed between neighboring protrusions of the plurality of protrusions and the channels extend continuously from the first edge of the base surface to the second edge of the base surface, a second direction being defined as perpendicular to the base surface, and a third direction being defined as perpendicular to the first direction and perpendicular to the second direction, wherein for at least of the plurality of protrusions, a distance measured along the third direction between the two protrusions in a plane substantially perpendicular to the first direction is smaller than a distance between the two protrusions at the base surface, and wherein a distance measured along the third direction between the two of the protrusions in a plane substantially perpendicular to the second direction at the first edge and the second edge is larger than a distance between the two protrusions in the same plane at a point between the first edge and the second edge.

15. A bracket comprising a base according to claim 14.

16. The base according to claim 14, wherein all of the plurality of protrusions are substantially identical.

17. The base according to claim 14, wherein one or more of the plurality of protrusions has, along its length, a linearly varying cross-section in the plane substantially perpendicular to the first direction.

18. The base according to claim 17, wherein a width of the plurality of protrusions varies linearly.

19. The base according to claim 18, wherein each of the plurality of protrusions has a widest cross-section in the plane substantially perpendicular to the first direction and the widest cross-section is located substantially midway between the first edge and the second edge.

20. The base according to claim 19, wherein each of the two protrusions has a bottom proximal the base surface and a top distal the base surface, and wherein a distance between the two protrusions in the plane substantially perpendicular to the first direction is minimum substantially at or near a top of the two protrusions.

* * * * *